United States Patent [19]

Allen et al.

[11] 4,258,227

[45] Mar. 24, 1981

[54] SHORT RESIDENCE HYDROPYROLYSIS OF RESIDUES FROM AROMATIC CARBOXYLIC ACID MANUFACTURE

[75] Inventors: John K. Allen; Agnes M. Palka, both of St. Charles, Ill.; Edward A. Lambers, Somerset, N.J.

[73] Assignee: Standard Oil Company (Indiana), Chicago, Ill.

[21] Appl. No.: 100,837

[22] Filed: Dec. 6, 1979

[51] Int. Cl.$^3$ .................................................. C07C 1/20
[52] U.S. Cl. ................................... 585/469; 562/479
[58] Field of Search ......................... 585/469; 562/479

[56] References Cited

U.S. PATENT DOCUMENTS

| | | | |
|---|---|---|---|
| 1,962,175 | 6/1934 | Daudt | 562/479 |
| 3,210,415 | 10/1965 | Berkey et al. | 562/479 |
| 3,862,145 | 1/1975 | Brennan et al. | 562/479 |

*Primary Examiner*—Curtis R. Davis

*Attorney, Agent, or Firm*—Fred R. Ahlers; William T. McClain; William H. Magidson

[57] ABSTRACT

Short, less than one second, residence time non-catalytic hydropyrolysis is conducted by rapid heating at more than 600° C. per second of a solid mixture of aldehydo-, carboxy-, keto- and carboxy-, and aldehydo- and carboxy- substituted benzene and toluene and such solid also containing cobalt and/or manganese salts of organic acids and organic and/or inorganic bromides obtained from the manufacture of benzene di- and tri-carboxylic acids up to a temperature of at least 700° C. Such short residence hydropyrolysis produces attractive amounts of readily recoverable benzene and toluene as well as lower alkanes and alkenes and a solid carbonaceous char which can be burned to provide heat for the hydropyrolysis. The short residence hydropyrolysis is not subject to short activity and frequent periods of off-stream time as are the catalytic pyrolysis conducted at lower temperatures of from 300° up to 500° C.

3 Claims, No Drawings

SHORT RESIDENCE HYDROPYROLYSIS OF RESIDUES FROM AROMATIC CARBOXYLIC ACID MANUFACTURE

FIELD OF INVENTION

The invention relates to the recovery of aromatic compound values from residues obtained in the manufacture of an aromatic di- or tricarboxylic acid. More specifically the present invention pertains to a short residence time hydropyrolysis conducted at an elevated temperature above 500° C. with a mixture of oxygen-containing derivatives of benzene and toluene containing a cyclic ester group (e.g., as in phthalide) and one or more aldehydo-, methylol-, carboxy-nuclear substituents.

STATE OF THE ART

The thermal decomposition of benzoic acid to benzene and carbon dioxide begins non-catalytically at 370° C. in a glass bulb and is substantially complete at 400° C. (Chemical Abstracts, vol. 41, 646) according to the original article of Wolfgang Mosher in Helv. Chem. Acta. 14, 971–97 (1931) and such dissociation is accelerated by copper and cadmium catalysts. Said dissociation occurs at temperatures as low as 245° to 250° C. in the presence of Zn—Cu—Cr oxide-type catalysts according to Corliss R. Kinney and David P. Langlois in J. Am. Chem. Soc. vol. 53, 2189–2192 (1931). Decarbonylation of benzaldehyde to high yields of benzene is aided by plasma of glow discharge according to German Published Patent Application ("Offenlegungschrift") No. 2,038,272 of the Federal German Republic published Mar. 16, 1972. According to British Pat. No. 735,300 published Aug. 17, 1955 toluic acids heated to 400° in the presence of chromites of Zn, Cd, Zn—Cd, Zn—Fe or ZnO with either CuO or CdO are converted to toluene.

The preparation of benzoic acid by the thermal decarboxylation of phthalic acids in the presence of steam is known to be generally conducted in the presence of a catalyst such as nickel phthalate at 175° to 350° C. according to U.S. Pat. No. 1,962,175; 1 to 2% ammonia in the steam according to British Pat. No. 469,541 published July 27, 1932; $V_2O_5$ or ZnO on $Al_2O_3$ or $Al_2O_3$ alone according to Chemical Abstracts vol. 37, Col. 5383; carbon catalyst impregnated with hydroxides of both alkali and alkaline earth metals to effect the decarboxylation at temperatures at and below 400° C. according to U.S. Pat. No. 2,470,688; cobalt carbonyl, $Co_2(CO)_8$ used in an atmosphere of carbon monoxide and hydrogen converts phthalic acids and substituted phthalic acids to benzoic acid and substituted benzoic acid or cobalt carbonyl modified by trialkylphosphine ligands converts benzene polycarboxylic acids having COOH groups on adjacent ring carbon atoms to iso- and terephthalic acids according to Chemical Abstracts vol 81 entry 52064r. Also heating trimellitic acid to temperatures of 300° to 375° C. converts the tricarboxylic acid to o-phthalic acid according to U.S. Pat. No. 3,862,145.

From the state of the art at the time of making the present invention it appears that the main interest in decarboxylation of benzene carboxylic acids was to prepare a higher quality benzene carboxylic acid of lesser COOH group content from a benzene carboxylic acid of higher COOH group content and lower quality such as a coal acid or to obtain a benzene carboxylic acid of exceptionally high quality; e.g., pharmaceutical quality benzoic acid, from phthalic anhydride by converting it to o-phthalic acid and decarboxylating it. But there was no apparent interest in the decarboxylation of benzene carboxylic acids to aromatic hydrocarbons.

In an altogether different environment a new problem has arisen. In the commercial manufacture of benzene di- or tricarboxylic acids (e.g., isophthalic acid, terephthalic acid or trimellitic acid) there is obtained, after maximizing recovery of such acid and recovery for reuse the reaction solvent, a residue which is a mixture of oxygen-containing derivatives of benzene and toluene which are mono-, di- and tricarboxylic acids, aldehydo-carboxylic acids, and methylol-substituted benzene or toluene or their carboxylic (benzoic or toluic) acids and which also contains components of catalysis. Usually such components of catalysis are Co—Mn—Br or Co—Mn—Ce—Br from liquid phase oxidation of a xylene or pseudocumene (1,2,4-trimethylbenzene) with air in the presence of acetic acid reaction solvent. A similar residue is also obtained from the next oxidation of liquid o-xylene with air in the presence of Co—Mn—Br catalyst system after dehydrating the o-phthalic acid formed to its anhydride under conditions which vaporizes the anhydride, water and materials boiling between the anhydride and water. While such residues amount to from 2 to 25 weight percent of the benzene di- or tricarboxylic acid produced, such residue production annually is substantial in view of the millions of kilograms of the benzene di- or tricarboxylic acids produced annually.

Such residues contain water soluble benzene carboxylic acids and water soluble forms of the components of catalysis. Landfill disposal of such residues is undesirable because rain and ground water leach out those carboxylic acids and soluble forms of the components of catalysis and can contaminate surface run off water and eventually streams as well as below surface aquafiers. Disposal of such residues can be made by incineration and use made of the resultant heat produced but the catalyst components are converted to forms in the resultant ash which are difficult and/or expensive to convert to reusable forms for the oxidation of the methyl-substituted benzenes. Although in such residues the substituted benzene and toluene compounds whose substituents are the carboxy-, aldehydo- and methylol substituents are individually desirable and useful commercial products it is not economically feasible to separate and recover the individual compounds from the residues.

Based on the knowledge that most of the oxygen-containing aromatic compounds in the residue can be decarboxylated and/or decarbonylated by thermal means, it would be desirable to devise a decarboxylation and/or decarbonylation process which would convert the oxygen-containing aromatic compounds to aromatic hydrocarbons which are volatile under such process conditions so that the hydrocarbon vapors can be readily removed and condensed for their recovery. It is also known that under the severe thermal conditions required for substantially complete decarboxylation and/or decarbonylation to convert the oxygen-containing substituted aromatics to benzene and toluene there can also occur ring coupling (e.g. to form biphenyl) and ring fusion as well as charing of some of the organic compounds.

To use a decarboxylation and/or decarbonylation catalyst for the thermal conversion of the foregoing residues to easily recoverable and useful aromatic hydrocarbons would be desirable providing the use of catalyst does enhance the production of the aromatic hydrocarbons but does not make useless the resulting char or further contaminate the catalyst components present so as to make the recovery of cobalt, the most expensive component, technically and commercially unattractive.

We have in our laboratories investigated the use of various compositions previously suggested as decarboxylation catalyst and found the resulting thermal conversions to be unattractive. However, the present inventive non-catalytic thermal conversion of the foregoing residues to useful aromatic hydrocarbons is technically and commercially attractive as a step in a route for disposal of such residues.

SUMMARY OF THE INVENTION

According to the present invention the aforementioned residue or the water-insoluble portion thereof from the manufacture of a benzene di- or tricarboxylic acid is quite rapidly heated to a temperature in the range of from 700° C. up to 900° C. for a short, less than one second down to 0.1 second, residence time in contact with a pressurized hydrogen atmosphere under pyrolysis conditions in the absence of a catalyst. By such short duration hydropyrolysis the aforementioned residue is converted into two hydrocarbon-containing products. The first product comprises in addition to carbon oxides and hydrogen the normal gaseous hydrocarbons methane, ethane and ethylene. The second product comprises mainly the normally liquid aromatic hydrocarbons benzene and toluene together with small amounts of biphenyl and lesser amounts of higher molecular weight multi-ring hydrocarbons containing two, three or more aromatic rings as in terphenyl, or anthracene. It is believed the contact between hydrogen gas and the decarboxylated and decarbonylated aromatic ring entities in the vapor state, although for a rather short time as well as in the absence of a catalyst, minimizes the formation of biphenyl and the multi-ring compounds.

Any feasible means for rapidly heating the residue to a temperature of from 700° C. up to 900° C. can be used. For example, small amounts of residue can be moved by belt, or screw, or paddle or bucket conveyor through a tube or tubes externally heated; e.g., by a furnace or a kiln in a hydrogen atmosphere. Heating the residue at a rate above 600° C. per second, for example, at 650° to 700° C. per second will provide adequately rapid heating for the purposes of this invention. The hydrogen gas atmosphere for the 700° to 900° C. temperature used in the hydropyrolysis process of the present invention can be in the range of from 80 up to 150 kg/cm² pressure. Suitable contact time between hydrogen and the decarboxylated and/or decarbonylated ring entities vaporized from the residue can be in the range of from 0.7 second down to 0.2 second.

The resulting mixture of gases and vapors from the present inventive hydropyrolysis are cooled to about 75° C. or below to condense the aromatic hydrocarbons as a liquid product. The uncondensed mixture comprises mainly oxides of carbon together with the hydrogen and some methane and even ethylene, ethane and propane.

The hydropyrolysis also produces a solid product, char, which contains catalyst metals, bromine if used for catalysis, but is mainly carbon with some hydrogen and oxygen. Unlike an incineration ash, the char can be extracted with acetic acid to remove most of the catalyst metals and, if present, a portion of the bromine. The extracted char together with the uncondensed gases can be burned as fuel to supply the heat for pyrolysis.

Residues from the manufacture of benzene di- and tricarboxylic acids in general contain from zero to five weight percent total of water and acetic acid, from three up to five weight percent total of components of catalyst and associated with the metals (usually in the plus two valence state) from three to ten weight percent acetate radical. Thus, the oxygen-containing aromatic compounds can comprise from 79 to 96 weight percent of the residue.

More specifically, the oxygen-containing aromatic compounds which can be present in the residues subjected to hydropyrolysis of this invention can be illustrated by the identified compounds present in the residue from the manufacture of terephthalic acid by the air oxidation of p-xylene in acetic acid as reaction solvent and in the presence of cobalt, manganese and bromine as components of the catalyst system. Such identified compounds are now known to be: terephthalic acid and its precursors p-toluic acid, p-formylbenzoic acid, p-tolualdehyde, terephthalaldehyde and p-methylbenzyl alcohol by-products including methylphthalic acids, ortho-and isophthalic acids (from o- and m-xylene impurities in the p-xylene), trimellitic acid, as well as benzaldehyde and benzoic acid (from ethylbenzene impurity in p-xylene); and co-products including 4,4'-bibenzoic acid; 1,2-bis(p-carboxyphenyl)ethane; 2,5,4'-tricarboxybiphenyl; 2,6-dicarboxyfluorenone; and 4,4'-stilbene dicarboxylic acid. On a water and acetic acid-free basis one such residue contains the weight percentages of the foregoing compounds and groups of compounds as shown in TABLE I to follow.

TABLE I

| COMPONENTS OF RESIDUE FREE OF OF WATER AND ACETIC ACID | |
|---|---|
| Terephthalic Acid | 26.4% |
| p-Toluic Aids | 20.8% |
| p-Formylbenzoic acid | 9.1% |
| p-Tolualdehyde | 0.51% |
| Terephthalaldehyde | 1.20% |
| p-Methylbenzyl Alcohol | 2.06% |
| Reaction By-Products | 36.9% |
| Co-Products | 4.12% |

Another such residue has the composition including the catalyst components: cobalt, manganese and bromine and metals or corrosion as shown in TABLE II to follow.

TABLE II

| RESIDUE FROM TEREPHTHALIC ACID MANUFACTURE ON ACETIC ACID AND WATER-FREE BASIS | |
|---|---|
| Component | Weight Percent |
| Phthalic Acids | 19.0 |
| Benzoic Acid | 14.8 |
| Toluic Acids | 26.7 |
| Methyl Phthalic Acids | 2.65 |
| Trimellitic and Trimessic Acids | 4.32 |
| 4-Carboxybenzaldehyde | 9.09 |
| Tolualdehydes | 0.40 |
| Benzaldehyde | 0.004 |
| Terephthalaldehyde | 0.27 |
| Methylbenzyl Acetate | 0.02 |
| Formyl Acetate | 0.15 |
| Benzylbenzoate | 0.07 |
| Phthalide | 2.04 |
| Co-Products | 4.24 |
| Cobalt | 1.51 |

TABLE II-continued

RESIDUE FROM TEREPHTHALIC ACID MANUFACTURE ON ACETIC ACID AND WATER-FREE BASIS

| Component | Weight Percent |
|---|---|
| Manganese | 2.53 |
| Bromine | 2.20 |
| Iron | 0.09 |
| Aluminum | 0.00022 |
| Calcium | 0.02 |
| Chromium | 0.007 |
| Copper | 0.0001 |
| Magnesium | 0.0028 |
| Molybdenum | 0.0035 |
| Sodium | 0.30 |
| Nickel | 0.0052 |
| Silica | 0.0025 |
| Anion of Metals | 9.04 |

The first four elements are determined by X-ray fluorescence and the remaining elements are determined by emission spectroscopy. The foregoing more detailed identification of organic components and metals is not one usually made by terephthalic acid manufacturing facilities but is made for research purposes as a starting point, for example, to identify extractable components, or to evaluate the completeness of commercial oxidation of the xylene feed, or to evaluate potential increase of phthalic acids production by some additional oxidation of the phthalic acid precursors present in such residue.

However, the terephthalic acid manufacturing facilities will obtain a partial analysis of the residue to include at least the phthalic acids, toluic acids, benzoic acid and catalyst components to determine on a day-to-day basis the approximate oxidation efficiency, and catalyst metal and solvent discard. Such partial analytical inspections of the residue are as shown in TABLE III to follow.

TABLE III

PARTIAL ANALYTICAL RESULTS OF RESIDUE FROM TEREPHTHALIC ACID MANUFACTURE

| Components In Weight % | Sample Number | | | |
|---|---|---|---|---|
| | 1 | 2 | 3 | 4 |
| Acetic Acid | 0.22 | 3.23 | 3.74 | 3.24 |
| Phthalic Acids | 45.8 | 31.4 | 33.4 | 26.0 |
| Toluic Acids | 5.2 | 12.3 | 12.8 | 22.6 |
| 4-CBA[1] | 1.05 | 4.56 | 4.82 | 9.1 |
| Benzoic Acid | 20.2 | 27.6 | 26.0 | 19.8 |
| Trimellitic Acid | 5.4 | 4.0 | 4.3 | 3.8 |
| OLB Compounds[2] | 5.4 | 4.1 | 4.4 | 0.9 |
| HB Compounds[3] | 0.26 | 7.5 | 5.8 | 0.4 |
| Cobalt | 0.69 | 0.49 | 0.5 | 1.35 |
| Manganese | 1.79 | 1.22 | 1.3 | 2.48 |
| Bromine | 2.59 | 1.49 | 1.5 | 2.5 |

[1]"4-CBA" is 4-carboxybenzaldehyde (p-formylbenzoic acid).
[2]"OLB Compounds" are other lower boiling compounds.
[3]"HB Compounds" are higher boiling (higher than trimellitic acid) compounds.

The residue from manufacture of isophthalic acid by air oxidation of m-xylene in an acetic acid reaction medium and in the presence of catalysis provided by cobalt, manganese and bromine is quite similar to the residue from the manufacture of terephthalic acid by the same oxidation of p-xylene. The manufacture of the anhydride (intramolecular) of trimellitic acid (TMA) can produce two residues. One residue is obtained after precipitating and separating impure trimellitic acid from the acetic acid solution of the catalyst (Co—Mn—Br) system and then evaporating the acetic acid. The second residue is obtained after dehydration of impure trimellitic acid (TMLA) to its impure anhydride and evaporating a partially purified anhydride. The compositions of such TMLA and TMA residues and the residue from isophthalic acid (IA) manufacture are characterized in TABLE IV to follow.

TABLE IV

CHARACTERIZATION OF RESIDUES FROM THE MANUFACTURE OF ISO-PHTHALIC ACID AND TRIMELLITIC ANHYDRIDE

| | RESIDUE | | |
|---|---|---|---|
| Component | IA | TMLA | TMA |
| In Weight % | | | |
| Acetic Acids | 0.11 | 1.58 | 0 |
| Phthalic Acids | 39.8 | 12.3 | 1.0 |
| Toluic Acids | 1.8 | 0 | 0 |
| Aldehydes | 0.09 | 0.53 | 1.4 |
| Benzoic Acid | 24.1 | 0.5 | 0 |
| Trimellitic Acid | 2.5 | 38.6 | 65.2[1] |
| OLB Compounds[2] | 1.7 | 4.7 | 1.9 |
| HB Compounds[3] | 5.3 | 0.94 | 0.4 |
| Cobalt | 0.48 | 1.17 | 2.51 |
| Manganese | 1.27 | 0.28 | 0.87 |
| Bromine | 2.6 | 0.94 | 0.15 |

[1]Trimellitic acid anhydride
[2]See TABLE III
[3]See TABLE III

The residues from the manufacture of phthalic anhydride of interest for use in the practice of the present invention are obtained from two different oxidation processes. The residue from the first of such processes is obtained after evaporation of acetic acid and water from the liquid portion of the oxidation effluent from the air oxidation of o-xylene in an acetic acid solution of the Co—Mn—Br catalyst system after precipitating and recovering o-phthalic acid or its anhydride from the oxidation effluent. Such residue contains the components and their concentrations substantially the same as in the residues characterized by TABLES I through III. The residue from the second type of oxidation process is obtained by heating the oxidation effluent to convert o-phthalic acid to its anhydride and evaporate the anhydride and water when such effluent is produced by the air oxidation of liquid o-xylene in liquid o-phthalic acid containing the Co—Mn—Br system of catalysis. Since such oxidation does not use an extraneous solvent, it is hereafter sometimes referred to as the "neat oxidation" process. Such residue from the second type of oxidation process comprises 50 to 85 weight percent phthalic anhydride as a flux for higher boiling materials; e.g., iso- and terephthalic acid, trimellitic acid, metal (Co and Mn) phthalates or acetates, and oxygen-containing both coupled and fused ring compounds: di-, tri- and tetracarboxy-substituted biphenyl and benzophenone and dicarboxyfluorenone. In TABLE V to follow there are given the components and their concentrations in weight percent of such residues from said second type of o-xylene oxidation process.

In TABLE V "PAN" is used to designate phthalic anhydride and "2-CBA" is used to designate 2-carboxybenzaldehyde.

TABLE V

NEAT OXIDATION RESIDUES

| Component Weight % | Residue Number | | | | |
|---|---|---|---|---|---|
| | 1 | 2 | 3 | 4 | 5 |
| PAN | 72.2 | 77.4 | 65.7 | 84.5 | 57.3 |
| o-Toluic Acid | 0.03 | 0.23 | 0.15 | 0.04 | 0.1 |
| Phthalide | 0.01 | 0.2 | 0.18 | 0.001 | 0.3 |
| 2-CBA | 0.77 | 1.0 | 1.03 | 0.41 | 1.65 |
| Benzoic Acid | 0.56 | 1.03 | 0.69 | 0.60 | 1.8 |
| Other Aromatics | 20.7 | 16.0 | 26.8 | 11.5 | 22.7 |
| Cobalt | 1.14 | 1.08 | 1.36 | 0.62 | 0.58 |
| Manganese | 3.38 | 2.29 | 3.34 | 1.85 | 1.13 |

TABLE V-continued

NEAT OXIDATION RESIDUES

| Component | Residue Number | | | | |
|---|---|---|---|---|---|
| Weight % | 1 | 2 | 3 | 4 | 5 |
| Bromine | 1.32 | 0.90 | 0.78 | 0.87 | 1.01 |

Also useful in the practice of the present inventive hydropyrolysis are the undissolved solids portion of the residues after the extraction of the residues with water to remove catalyst metals for reuse in the oxidation from which the metal-containing residue originated. Such undissolved solids portion is hereafter referred to as "extracted residue." In TABLE VI to follow characteristics of such extracted residues are given.

TABLE VI

EXTRACTED RESIDUES

| Components Weight % | Of Sample 1 TABLE III | Of Sample 3 TABLE III | of Neat Oxidn. Residue |
|---|---|---|---|
| Aldehydes | 1.57 | 5.84 | 1.03 |
| Benzoic Acid | 18.1 | 31.4 | 1.7 |
| Toluic Acids | 1.61 | 16.0 | 0 |
| Phthalic Acids | 56.4 | 37.6 | 5.6 |
| OLB Compounds | 0.4 | 0.78 | 41.0 |
| HB Compounds | 8.0 | 3.6 | 0.2 |
| Cobalt | 0.18 | 0.03 | 0.16 |
| Manganese | 0.49 | 0.10 | 0.28 |
| Bromine | 0.51 | 0.09 | 0.35 |

There follows in TABLES VII and VIII the results of vapor phase decarboxylation of a single benzene carboxylic acid by vaporizing the acid at one temperature and then contacting the vapors with a catalyst sometimes at a second temperature as indicated. Further, in such decarboxylation the catalyst is first placed in a quartz tube, the tube is heated in two zones with electric furnaces, and the benzene carboxylic acid sample is inserted into the vaporizing section of the tube in a ceramic boat, said boat is moved into and out of the vaporizing portion of the tube by a nichrome wire attached to the boat. Vaporization of the sample is accomplished in 5 to 15 minutes at the 500° C. temperature. A small nitrogen gas flow (about 3 ml/sec) through the tube is used to sweep the vapors through the hot catalyst and out of the tube. Products of the decarboxylations are collected by transport of the gaseous mixture after contact with the catalyst through two cooled traps, then through a drier to remove water vapor and then to a gas collector. At least one of the traps is cooled with a mixture of crushed solid $CO_2$ and isopropyl alcohol. Measured samples of the collected gas are analyzed by mass spectrometry. For the present purpose of illustrating the effectiveness of prior suggested catalysts, only the total amount of liquid aromatic hydrocarbons collected in the cooled traps and the amount of $CO_2$ generated expressed as weight percentages of the benzene carboxylic acid used are reported.

Except for two decarboxylations in TABLE VII illustrating the use of zinc oxide and zinc oxide supported on alumina as the catalyst, the benzene carboxylic acid samples subjected to decarboxylation were about one gram in size. Those two exceptions used five gram samples supplied by five one gram samples successively introduced into the vaporizing portion of the tubes.

TABLE VII

DECARBOXYLATION OF TEREPHTHALIC ACID

| | | Temperature, °C. | | Product, Wt. % | |
|---|---|---|---|---|---|
| | Catalyst | Vap. | Catalyst | Liquid | $CO_2$ |
| 4789-151 | Ba Promoted Cu Chromite | 352 | 352 | 3.97 | 64.5 |
| -150 | " | 399 | 399 | 7.99 | 127.7 |
| -156 | $Cu_2O_3$-Zno | 400 | 400 | 11.9 | 102.3 |
| -147 | Ni Oxide on Alumina | 446 | 446 | 18.0 | 45.4 |
| -155 | ZnO | 511 | 511 | 24.0 | 39.9 |
| -165 | ZnO-Chromia | 499 | 499 | 35.8 | 49.2 |
| -184 | Zn Chromite | 499 | 499 | 21.8 | 67.9 |
| -185 | Chromia-Alumina-Magnesia | 500 | 500 | 17.7 | 46.3 |
| -188 | K Promoted Chromia-Alumina | 499 | 499 | 20.8 | 66.1 |
| -195 | ZnO-Alumina | 498 | 498 | 33.9 | 29.0 |
| -200 | Zno-$MoO_2$ on Molecular Sieve | 499 | 499 | 31.7 | 26.8 |
| -204 | ZnO-$Co_2O_3$-$W_2O_3$ on Molecular Sieve | 500 | 500 | 33.0 | 48.8 |
| 5065-001 | Zn0-$Co_2O_3$-$MoO_2$ on Molecular Sieve | 500 | 500 | 22.0 | 39.3 |
| -005 | Chromia on Molecular Sieve | 499 | 499 | 17.0 | 41.3 |
| -006 | ZnO* | 501 | 501 | 24.3 | 23.0 |
| -007 | ZnO on Alumina* | 500 | 500 | 32.9 | 36.3 |
| -010 | ZnO-Alumina | 500 | 500 | 33.0 | 47.9 |
| -022 | " | 499 | 498 | 36.9 | 47.3 |
| -023 | " | 501 | 399 | 0 | 19.9 |
| -025 | " | 500 | 451 | 26.9 | 40.6 |
| -030 | CaO | 500 | 502 | 25.9 | 0.04 |
| -031 | $CaCO_3$ | 499 | 501 | 5.0 | 29.9 |
| -036 | CdO | 502 | 22.0 | 38.8 | |

*Five grams terephthalic acid

The theoretical amounts of benzene and carbon dioxide from the complete decarboxylation of terephthalic acid are, respectively, 47 weight percent and 53 weight percent. The above amounts of $CO_2$ reported in excess of said 53 wt.% may be from partial combustion of the benzene produced.

TABLE VIII

DECARBOXYLATION AND/OR DECARBONYLATION OF BENZOIC ACID AND SUBSTITUTED BENZOIC ACIDS IN THE PRESENCE OF ZINC OXIDE ON ALUMINA

| | | Temperature, °C. | | Product, Wt. % | |
|---|---|---|---|---|---|
| | Acid | Vap. | Catalyst | Liquid | $CO_2$ |
| 4789-149 | Benzoic Acid* | 399 | 399 | 19.9 | 12.26 |
| 5065-037 | Benzoic Acid | 501 | 501 | 53 | 29.7 |
| -011 | Isophthalic Acid | 500 | 500 | 33 | 45.4 |
| -012 | o-Phthalic Acid | 497 | 499 | 24 | 37.2 |
| -014 | p-Toluic Acid | 501 | 501 | 21 | 21 |
| -015 | Trimellitic Acid | 502 | 502 | 13 | 32.8 |
| -016 | 4-Carboxybenzaldehyde | 500 | 500 | 18.4 | 31.1 |
| -017 | Phthalic Anhydride | 502 | 502 | 20 | 36 |
| -035 | Trimellitic Acid Anhydride | 499 | 500 | 12.8 | 53.2 |

*Catalyst is Ni Oxide on Alumina

In TABLE IX to follow terephthalic acid process residue (TAR) unextracted or water extracted (TARX) is decarboxyl- and decarbonylated in the presence of various catalysts at various temperatures. Again only the total liquid aromatic hydrocarbons and $CO_2$, both in weight percent of sample, are reported. Also a slight flow (about 3 ml/sec) of nitrogen gas is used for the purposes before described.

TABLE IX
DECARBOXYLIC AND DECARBONYLATION OF TEREPHTHALIC ACID PROCESS RESIDUES

| Catalyst | | Temperature, °C. | | Product, Wt. % | |
|---|---|---|---|---|---|
| | | Vap. | Catalyst | Liquid | $CO_2$ |
| 4789-124 | Copper Wool | 353 | 353 | 0 | 2.29 |
| -125 | $Cu_2O$-wire | 350 | 350 | 0 | 10 |
| -126 | " | 400 | 400 | 0 | 16.6 |
| -134 | Ba Promoted Cu Chromite | 500 | 500 | 0 | 105.6 |
| -132 | Gamma Alumina | 500 | 500 | 0 | 19.8 |
| -128 | Chromia on Gamma Alumina | 400 | 400 | 0 | 14.5 |
| -136 | ZnO-Alumina Co Gel | 500 | 500 | 0 | 3.58 |
| -137 | Chromia Promoted $Fe_2O_3$ | 400 | 400 | 0 | 18.4 |
| -131 | Co-Molybdate on Gamma Alumia | 397 | | 0 | 1.64 |
| -142 | $Co_2O_3$ on Keiselguhr | 398 | 398 | 0 | 30.34 |
| -145 | Ni Oxide on Refractory Support | 399 | 399 | 10.96 | 15.8 |
| -171 | ZnO | 499 | 499 | 28.0 | 23.4 |
| -196 5065-009 | ZnO on Alumina (1) | 500 | 500 | 26.0 | 22 |
| -008 | ZnO on Alumina (1,2) | 499 | 499 | 26.2 | 30.0 |
| -041 | ZnO on Alumina (3) | 502 | 502 | 27.7 | 26.2 |
| -044 | ZnO on Alumina (4) | 501 | 501 | 24.0 | 26.7 |
| -026 | ZnO on Alumina (2) | 501 | 501 | 28.0 | 31.0 |
| | ZnO on Alumina | 501 | 502 | 30 | 35.8 |
| -027 -034 | ZnO on Alumina (5) | 503 | 500 | 26 | 36.4 |
| | ZnO on Alumina | 499 | 504 | 22.9 | 40.4 |

(1)Sample is five grams
(2)Residue from terephthalic acid process after beingextracted with water.
(3)Sample is 40.76 grams
(4)Sample is 28.85 grams
(5)Residue from o-phthalic acid process after beingextracted with water.

In general, the use of prior suggested decarboxylation catalysts did cause carbon dioxide to be liberated or produced but not all such catalysts caused an attractive co-production of liquid aromatic hydrocarbons. Of those prior suggested decarboxylation catalysts Zinc oxide alone; or zinc oxide in admixture with or supported by chromia or alumina; or a mixture of zinc oxide with either molybdena, or with oxides of cobalt and tungsten supported on molecular sieves in general were found to produce liquid aromatic hydrocarbons in yields upward from about 50 percent of the theoretical yield at temperatures above 450° C. However, the effective life of such better liquid aromatic hydrocarbon producing catalyst was short.

The consistently better prior suggested catalyst was found to be the combination of zinc oxide and alumina. Such catalyst is used at 500° C. with one to two gram samples of terephthalic acid process residues introduced consecutively at about 5-minute intervals into the heated quartz tube containing said catalyst over a five day period. The liquid aromatic hydrocarbon yield decreases from 26.4 weight percent down to 14.6 weight percent of residue fed over the five day period and considerable blackening of the catalyst is observed. Said liquid aromatic hydrocarbon decrease occurs with a residue to catalyst weight ratio of no more than about 2:1. Such results indicate a very short life for the ZnO-alumina catalyst and that frequent regeneration thereof would be necessary for such catalyst to be used commercially.

Thus, non-catalytic pyrolysis of the before described residues from benzene di- and tricarboxylic acid manufacture would be more attractive commercially, provided the yield of liquid aromatic hydrocarbons would be equal to or better than the liquid aromatic hydrocarbon yield from the long term (five day) test of the ZnO on alumina catalyst.

The conduct of the illustrative non-catalytic hydropyrolysis to follow are conducted in apparatus devised for small scale operation of the present inventive hydropyrolysis. Said apparatus comprises: a tubular reactor which is a 316 stainless steel tube 304.8 mm long having a 6.35 mm outside diameter and a 1.245 mm wall thickness. Two type K thermocouple wires are spot welded to the center of the tube. One thermocouple is connected to a high temperature cut-off control and the other thermocouple is connected to a temperature recorder. The tube is heated by two copper electrodes each having a groove of the tubes' curvature to which the reactor tube is clamped by grooved brackets. During operation only 203 mm (101.5 mm each side of center) of the tube is heated. Power is supplied to the electrodes by a first transformer and timer combination to heat the tube at a rate of 650° C./sec. The second transformer provides a more gradual heating over a 4 second period to the final temperature. The reactor tube is adapted at one end to be attached to a metered supply of compressed hydrogen through pressure control valves and at the other end to be attached to a gas chromatograph column 3.175 mm internal diameter and 1219 mm long packed with Poropak Q. Analysis of the products is accomplished by cooling the column with liquid nitrogen to 15° C.

The reactor tube is packed with quartz wool 146 mm from the center on the discharge portion of the tube. The sample (4 to 10 mg), preferably ground to 270 mesh (U.S. Standard Sieve Size) or less, is inserted from the inlet end of the tube and deposited on the front face of the quartz wool plug. Quartz wool is then loosely packed into 152 mm of the inlet length from the center of the tube. The packed tube is then inserted into the flow system and compressed hydrogen is passed through the gas chromatograph.

The illustrative examples use terephthalic acid process residue (TAR) and insolubles (TARX) remaining after water extraction of such residue. Said insolubles were, of course, dried before use in the present inventive process. TABLE X provides the operating conditions of, and TABLE XI provides the results from the hydropyrolysis of the unextracted residue (TAR) and the extracted residue (TARX).

TABLE X
OPERATING CONDITIONS FOR THE HYDROPYROLYSIS

| Example | | Feed | | Temperature, °C. | |
|---|---|---|---|---|---|
| | Number | Type | Mg. | °C./sec. | Max. |
| May 78 Mo.PR | 1 | TARX | 11.6 | 697 | 895 |
| 4667-061B6 | 2 | TARX | 4.8 | 703 | 830 |
| -061B5 | 3 | TARX | 7.8 | 661 | 805 |
| -061B1 | 4 | TARX | 9.7 | 703 | 703 |
| -061B4 | 5 | TARX | 5.4 | 726 | 867 |
| -1753 | 6 | TAR | 9.6 | 714 | 873 |
| -1754 | 7 | TAR | 7.9 | 727 | 869 |
| -1756 | 8 | TAR | 7.8 | 738 | 897 |
| -1755 | 9 | TAR | 7.8 | 709 | 879 |
| -061B3 | 10 | TAR | 13.0 | 678 | 822 |

TABLE X-continued

OPERATING CONDITIONS FOR THE HYDROPYROLYSIS

| -061B | 11 | TAR | 12.6 | 661 | 810 |
|---|---|---|---|---|---|

| Example Number | $H_2$ Press. $kg/cm^2$ | VRT, sec. |
|---|---|---|
| 1 | 107.6 | 0.27 |
| 2 | 105.5 | 0.34 |
| 3 | 105.5 | 0.34 |
| 4 | 108.3 | 0.4 |
| 5 | 105.5 | 0.4 |
| 6 | 105.5 | 0.4 |
| 7 | 105.5 | 0.4 |
| 8 | 107.6 | 0.45 |
| 9 | 105.5 | 0.5 |
| 10 | 109.7 | 0.66 |
| 11 | 108.3 | 0.66 |

TABLE XI

RESULTS OF THE HYDROPYROLYSIS
Hydrocarbon Products, wt. %

| Examples Number | Aromatic | | Alkane | | |
|---|---|---|---|---|---|
| | $C_6H_6$ | $C_7H_8$ | $CH_4$ | $C_2H_6$ | $C_3H_8$ |
| 1 | 24.7 | 6.5 | 5.1 | 2.0 | 1.3 |
| 2 | 23.7 | 5.5 | 3.6 | 2.5 | ND |
| 3 | 14.8 | 5.9 | 2.2 | 1.2 | ND |
| 4 | 15.6 | 5.5 | 2.3 | 2.0 | ND |
| 5 | 23.2 | 5.9 | 3.9 | 3.6 | ND |
| 6 | 17.3 | 3.6 | 3.1 | 2.0 | ND |
| 7 | 18.9 | 4.5 | 3.5 | 3.4 | 1.5 |
| 8 | 18.8 | 2.8 | 4.4 | NM | NM |
| 9 | 15.8 | 2.9 | 2.9 | NM | NM |
| 10 | 20.6 | 2.5 | 4.4 | NM | NM |
| 11 | 23.0 | 8.4 | 0.15 | NM | NM |

"ND" is not detected.
"NM" is not measured.

The invention claimed is:

1. A method of decarboxylating and decarbonylating the mixture of oxygen-containing aromatic compounds and organic acid salts of cobalt and/or manganese obtained as a residue in the manufacture of a benzene di- or tricarboxylic acid by the liquid phase oxidation of a di- or trialkylbenzene in the presence of catalysis provided by the combination of bromine and one or both of cobalt and manganese or the insoluble mixture of catalyst metal-free oxygen-containing aromatic compounds obtained by extracting with water the catalyst metals from said residue, which method comprises heating said residue or the water-insoluble portion thereof to a temperature of from 700° C. up to 900° C. at a rate of above 600° C. per second in the presence of hydrogen gas under a hydrogen pressure of from 80 up to 150 $kg/cm^2$ for a vapor-gas residence time of less than one second down to 0.1 second whereby there is formed a hydrocarbon product including vapors of benzene and toluene together with the lower alkanes mixed with hydrogen and oxides of carbon; and collecting at least the vapors of benzene and toluene.

2. The method of claim 1 wherein the residue or water-insoluble portion thereof is obtained from the manufacture of terephthalic acid.

3. The method of claim 2 wherein the rate of heating is from 660° C. up to 740° C. per second to a maximum of from 700° to 900° C. and the vaporized materials are in contact with hydrogen for a residence time of from 0.27 up to 0.66 seconds.

* * * * *

UNITED STATES PATENT OFFICE
CERTIFICATE OF CORRECTION

Patent No. 4,258,227            Dated March 24, 1981

Inventor(s) John K. Allen, Agnes M. Palka and Edward A. Lambers

It is certified that error appears in the above-identified patent and that said Letters Patent are hereby corrected as shown below:

| Patent Column | Line | |
|---|---|---|
| 1 | 7 | "The" should be --This-- |
| 1 | 36 | "$400°$" should be --$400°C$-- |
| 1 | 50-51 | "$Co_2(-CO)_8$" should be --$Co_2(CO)_8$-- |
| 2 | 17-18 | "M-n" should be --Mn-- |
| 2 | 21 | "next" should be --neat-- |
| 2 | 25 | "vaporizes" should be --vaporize-- |
| 2 | 47 | "methylol substituted" should be --methylol-substituted-- |
| 4 | 38-39 | "FREE OF OF WATER" should be --FREE OF WATER-- |

UNITED STATES PATENT OFFICE
CERTIFICATE OF CORRECTION

Patent No. 4,258,227      Dated March 24, 1981

Inventor(s) John K. Allen, Agnes M. Palka and Edward A. Lambers

It is certified that error appears in the above-identified patent and that said Letters Patent are hereby corrected as shown below:

| Patent Column | Line | |
|---|---|---|
| 4 | 41 | "p-toluic aids" should be --p-toluic acid-- |
| 4 | 50 | "metals or" should be --metals of-- |
| 5 | 63 | "M-n" should be --Mn-- |
| 8 | 9 | "Zno" should be --ZnO-- |
| 8 | 34 | "-036CdO 502  22.0  38.8" should be ---036CdO 499 502 22.0 38.8-- |
| 9 | 5 | "DECARBOXYLIC" should be --DECARBOXYLATION-- |
| 9 | 20 | "Gamma Alumia" should be --Gamma Alumina-- |

UNITED STATES PATENT OFFICE
CERTIFICATE OF CORRECTION

Patent No. 4,258,227      Dated March 24, 1981

Inventor(s) John K. Allen, Agnes M. Palka and Edward A. Lambers

It is certified that error appears in the above-identified patent and that said Letters Patent are hereby corrected as shown below:

| Patent Column | Line | |
|---|---|---|
| 9 | 37 | "beingextracted" should be --being extracted-- |
| 9 | 39 | "beingextracted" should be --being extracted-- |
| 10 | 21 | "tubes'" should be --tube's-- |

Signed and Sealed this

Eighteenth Day of August 1981

[SEAL]

Attest:

GERALD J. MOSSINGHOFF

Attesting Officer      Commissioner of Patents and Trademarks